United States Patent
Swan et al.

(10) Patent No.: US 7,965,983 B1
(45) Date of Patent: Jun. 21, 2011

(54) METHOD AND SYSTEM FOR CONVEYING MEDICAL INFORMATION TO A MEDICAL SERVICE PERSON

(75) Inventors: Tim Swan, Lees Summit, MO (US); David McKinney, Olathe, KS (US)

(73) Assignee: Sprint Spectrum L.P., Overland Park, KS (US)

( * ) Notice: Subject to any disclaimer, the term of this patent is extended or adjusted under 35 U.S.C. 154(b) by 1142 days.

(21) Appl. No.: 11/633,236

(22) Filed: Dec. 4, 2006

(51) Int. Cl.
*H04B 7/00* (2006.01)

(52) U.S. Cl. ............ 455/41.2; 455/41.1; 455/41.3; 455/414.1; 455/414.2; 455/414.3

(58) Field of Classification Search .... 455/414.2–414.4, 455/41.1–41.3; 705/2, 3; 128/903–904
See application file for complete search history.

(56) References Cited

U.S. PATENT DOCUMENTS

| | | | |
|---|---|---|---|
| 2001/0044732 A1 | 11/2001 | Maus et al. | |
| 2002/0065625 A1 | 5/2002 | Xydis | |
| 2002/0103765 A1* | 8/2002 | Ohmori | 705/67 |
| 2002/0118112 A1* | 8/2002 | Lang | 340/573.1 |
| 2003/0130867 A1* | 7/2003 | Coelho et al. | 705/2 |
| 2004/0009750 A1 | 1/2004 | Beros et al. | |
| 2004/0127774 A1 | 7/2004 | Moore et al. | |
| 2004/0140898 A1 | 7/2004 | Reeves | |
| 2004/0193905 A1* | 9/2004 | Lirov et al. | 713/193 |
| 2005/0043827 A1 | 2/2005 | Schaeffer et al. | |
| 2005/0065822 A1 | 3/2005 | Ying et al. | |
| 2005/0105734 A1* | 5/2005 | Buer et al. | 380/270 |
| 2005/0159107 A1 | 7/2005 | Mauney et al. | |
| 2005/0174975 A1 | 8/2005 | Mgrdechian et al. | |
| 2005/0277872 A1 | 12/2005 | Colby, Jr. et al. | |
| 2005/0281237 A1 | 12/2005 | Heinonen et al. | |
| 2005/0285740 A1 | 12/2005 | Kubach et al. | |
| 2006/0030263 A1 | 2/2006 | Seligmann et al. | |
| 2006/0064472 A1 | 3/2006 | Mirho | |
| 2006/0252998 A1* | 11/2006 | Kimbrell | 600/300 |

\* cited by examiner

*Primary Examiner* — Jinsong Hu
*Assistant Examiner* — Dung Hong

(57) ABSTRACT

A method and system for securely conveying patient medical information to a medical service person is described. The conveyance may be conditional upon authentication of a unique code associated with a patient apparatus and a unique code associated with a medical service person apparatus. The patient medical information may be stored in a network server accessible by a medical information provider and conveyed in encrypted form to a medical service person apparatus via a patient apparatus. The medical information may be conveyed to the patient apparatus via a cellular communication and then conveyed to the medical service person's apparatus via a short-range direct wireless connection such as BLUETOOTH or Wi-Fi. Once present on the medical service person's apparatus, the medical information may decrypted and displayed.

17 Claims, 3 Drawing Sheets

METHOD AND SYSTEM FOR CONVEYING MEDICAL INFORMATION TO A MEDICAL SERVICE PERSON

FIELD OF THE INVENTION

The present invention relates to network communications and, more particularly, to conveying of information such as medical information to an apparatus such as a portable apparatus operated by a medical service person.

BACKGROUND

When a person is in a medical emergency situation, it may be necessary to convey medical information about the person to an attending medical service person, such as an emergency medical technician (EMT). One way to do so is for the person to carry a smart card or the like that is encoded with the person's medical information. Unfortunately, however, people do not generally carry such cards. Furthermore, carrying such a card risks the possibility of losing the card and potentially revealing private medical information to unauthorized parties. Consequently, an improved process is desired.

SUMMARY

The present invention provides a mechanism for securely conveying medical information regarding a patient to a medical service person. In accordance with an exemplary embodiment of the invention, the patient's medical information will be stored in a network server and be conveyed to the medical service person through a secure communication process via an apparatus possessed by the patient.

The secure communication process will involve the patient's apparatus receiving via short-range wireless communication from the medical service person's apparatus a code associated with the medical service person's apparatus and sending via a wireless wide area network connection to the network server both the code received from the medical service person's apparatus and a code associated with the patient's apparatus. The network server will then use those codes to validate both the patient's apparatus and the medical service person's apparatus and, upon successful validation, will send the patient's medical information via the wireless wide area network connection to the patient's apparatus, preferably in encrypted form. Once the patient's apparatus receives the encrypted medical information, it will then send that information over the short-range wireless connection to the medical service person's apparatus. The medical service person's apparatus will then decrypt and present the information to the medical service person.

In practice, the medical service person's apparatus will thus contain a code associated with the medical service person's apparatus, and will further have a decryption key for decrypting received information. The code and decryption key could be one element, possibly encrypted to prevent plain text viewing. Further, the medical service person's apparatus will include a short-range wireless transceiver (e.g., Wi-Fi, BLUETOOTH, etc.) and will be programmed to seek association with any corresponding nearby patient's apparatus, e.g., upon request from the medical service person. The short-range wireless transceiver may be programmed to associate with another apparatus operating under a predefined passkey/SSID; in this regard, the association can be peer-to-peer or client-server in nature (with the medical service person's apparatus being client or server). The medical service person's apparatus will further include program logic to carry out aspects of the inventive communication.

The patient's apparatus will similarly contain a code associated with the patient's apparatus, and the patient's apparatus will include a short-range wireless transceiver and program logic for correspondingly communicating with the short-range wireless transceiver of the medical service person's apparatus, under the predefined passkey/SSID, and with peer-to-peer or client-server communication. The patient's apparatus will also have a wide-area wireless transceiver (e.g., a cellular transceiver) for communicating via a WWAN radio access network with the network server. The patient's apparatus will further include program logic to carry out aspects of the inventive communication.

The network server will hold various patients' medical information and will indicate, for each patient's medical information, the patient apparatus' code, which can be provisioned into the network server at the time the patient acquires the apparatus—such as during service activation for instance. Further, the network server will hold the medical service person's apparatus' code. And the network server will include program logic for carrying out aspects of the inventive communication.

In operation, once the medical service person's apparatus establishes short range wireless association with the patient's apparatus, the medical service person's apparatus will convey to the patient's apparatus the medical service person's apparatus' code (preferably encrypted). This can be done by pushing or pulling. The patient's apparatus may then establish an access token by combining together the medical service person's apparatus' code (received from the medical service person's apparatus) and the patient's apparatus' code (possibly encrypting the combination). And the patient's apparatus will send that access token via the WWAN connection to the network server, with a request for patient medical information.

The network server will then validate the two unique codes, to ensure (i) that the medical service person's apparatus is an apparatus authorized to get the patient's data and (ii) that the patient's apparatus is indeed this patient's apparatus (i.e., the apparatus associated with the medical information at issue). Upon successful validation, the network server will then send the patient's medical information in response to the patient's apparatus' request, but the patient medical information will preferably be encrypted to prevent plain-text viewing at the patient's apparatus or elsewhere. The patient's apparatus will then send the encrypted patient's medical information via the short-range wireless connection to the medical service person's apparatus. The medical service person's apparatus will then apply the decryption key to decrypt the received medical information and will preferably present the medical information to the medical service person for use in serving the patient.

These as well as other aspects, advantages, and alternatives, will become apparent to those of ordinary skill in the art by reading the following detailed description, with reference where appropriate to the accompanying drawings. Further, it should be understood that the foregoing summary, like the other description provided below, is intended to illustrate the invention by way of example only and not by way of limitation.

DETAILED DESCRIPTION

1. System Architecture

Figure 1:
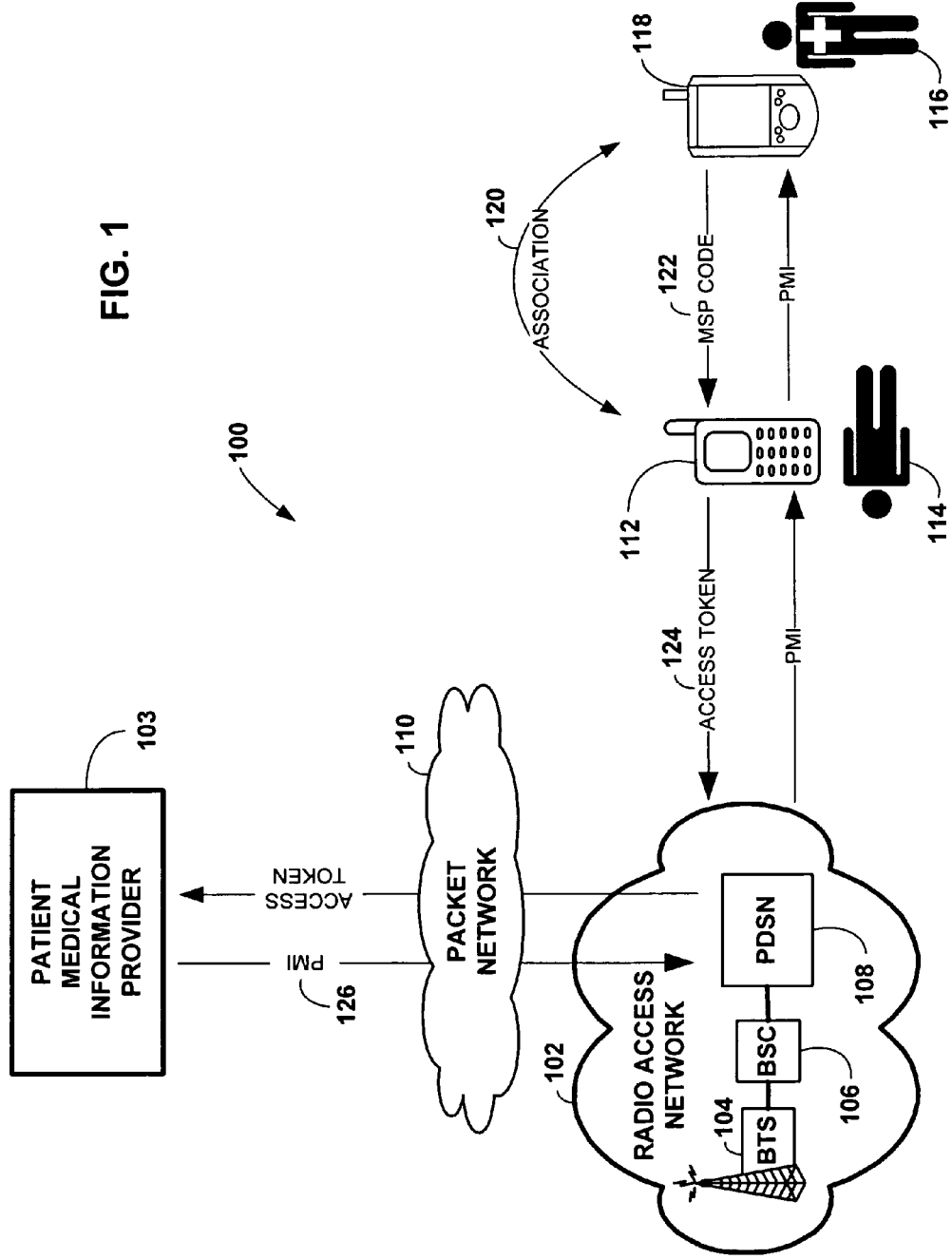
FIG. 1 is a simplified block diagram of a communication network in which examples of the present invention can be implemented.

Referring to the drawings, FIG. 1 is a simplified block diagram of an exemplary wireless communication system 100. It should be understood, however, that this and other arrangements and processes described herein are set forth for purposes of example only. Other arrangements and elements (e.g., machines, interfaces, functions, orders of elements, etc.) can be added or used instead and some elements may be omitted altogether. Further, as in most telecommunications applications, those skilled in the art will appreciate that many of the elements described herein are functional entities that may be implemented as discrete components or in conjunction with other components, in any suitable combination and location, and by hardware, firmware, and/or software (e.g., one or more processors programmed with machine language instructions to carry out the functions described).

Exemplary system 100 includes at its core a radio access network (RAN) 102, which provides connectivity between one or more mobile apparatuses and one or more transport networks. RAN 102 includes a base transceiver station (BTS) 104 that radiates to produce a cellular air interface coverage area (not shown) in which mobile devices can operate. (As used herein, the term "cellular" contemplates WWAN technology such as CDMA, TDMA, AMPS, GSM, or other such technologies now known or later developed.)

FIG. 1 further depicts a mobile patient apparatus (shown as a cellular telephone) 112 possessed by a patient 114 who may require emergency care by a medical service person 116. Patient apparatus 112 may be a multi-mode apparatus which includes both WWAN communication capability and short-range direct wireless communication capability such as BLUETOOTH, Wi-Fi, or other such technologies now known or later developed. (As used herein, the term "Wi-Fi" contemplates any WLAN communication technology now known or later developed.) Patient apparatus 112 may therefore communicate or exchange data via both short-range direct wireless communication and cellular communication. The patient apparatus 112 may also contain a decryption key for decrypting received information. The decryption key may be a master decryption key capable of decrypting a variety of content.

FIG. 1 also depicts a medical service person (MSP) apparatus (shown as a personal digital assistant (PDA)) 118 possessed by a medical service person 116. The MSP apparatus 118 is in proximity to the patient's apparatus 112. The MSP apparatus 118 includes short-range direct wireless connection capability such as BLUETOOTH, Wi-Fi, or other such technologies now known or later developed. MSP apparatus 118 may therefore communicate and/or exchange data via short-range direct wireless connection. The MSP apparatus 118 may also contain a decryption key for decrypting received information. The decryption key may be a master decryption key capable of decrypting a variety of content relating to a variety of patients.

Within RAN 102, BTS 104 is coupled with a base station controller (BSC) 106 which connects to a packet data serving node (PDSN) 108. The PDSN 108 provides connectivity with a packet-switched network 110, which may connect with a remote patient medical information (PMI) provider 103. The PMI provider 103 may comprise a network server.

The MSP apparatus 118 can be arranged to receive patient medical information concerning the patient 114 from the PMI provider 103 through a communication path comprising the patient's mobile apparatus 112, BTS 104, BSC 106, PDSN 108, and packet-switched network 110.

Note that many variations on the system of FIG. 1 are possible. For example, although the figure shows only one BTS, one BSC, and one PDSN, system 100 could include multiples of these entities. That is, a PDSN could serve one or more BSCs, each BSC could serve one or more BTSs, and each BTS could radiate to provide one or more coverage areas. As another example, the functional components of RAN 102 could be combined together in various ways. For instance, BTS 104 and BSC 106 could be combined together. As still another example, one or more of the functional components shown in the figure could be omitted altogether.

Although the apparatuses 112 and 118 are shown in FIG. 1 as a cellular telephone and a PDA respectively, the system could operate equally well with other sorts of mobile devices as well, such as wirelessly-equipped PDAs in the possession of the patient 114, or wirelessly-equipped personal computers in the possession of either party. Additionally, the apparatuses 112 and 118 may be dedicated devices without the additional features normally associated with, for example, a cellular phone or a PDA. For example, the mobile patient apparatus 112 could be an electronic bracelet or wearable device dedicated to facilitating the methods and systems described here. As another example, the MSP apparatus 118 could be a dedicated unit built into the structure of an emergency response vehicle such as an ambulance.

As used here, the term possession, or any variant of "possess," is not meant to exclusively indicate physical possession of an apparatus. While the term possession may indicate actual physical control of an apparatus by a person, it may also indicate that the apparatus is associated with the person and merely within the near proximity of the person. For example, a cellular phone possessed by the patient may be in the patient's home when the patient suffers a heart attack in her home. In another example, a patient may drop her cellular phone in the street during a heart attack and the phone would still be considered possessed by the patient. Further, note that "mobile apparatus" is a term of art that can encompass any wireless communication apparatus, regardless of whether the apparatus is easily movable (e.g. portable) or is located in a fixed position.

2. Example Device

Figure 2:
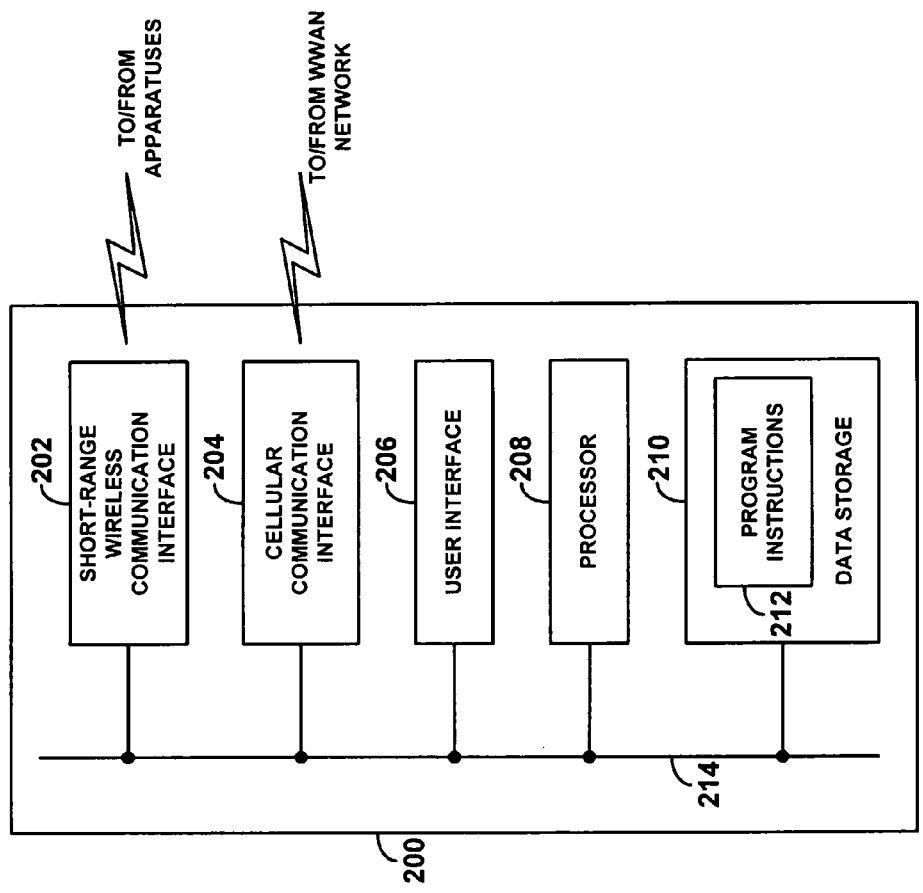
FIG. 2 is a simplified block diagram showing various functional components that a personal communication device may include.

FIG. 2 is a simplified block diagram showing various functional components that a personal communication device such as either of apparatuses 112 and 118 may include. As shown in FIG. 2, a personal communication device 200 includes a short-range wireless communication interface 202, a cellular communication interface 204, a user interface 206, a processor 208, and data storage 210, all of which are coupled together by a system bus or other mechanism 214. MSP apparatus 118 may or may not include the cellular communication interface 204. Although the components of device 200 are shown within one unitary box, it should be understood that the components can instead be distributed among various physically separate entities.

Short-range wireless communication interface 202 may be used to accomplish direct wireless communication with other apparatuses and it may comprise an 802.11 chipset and antennas adapted to facilitate Wi-Fi air interface communication with other Wi-Fi enabled devices. Short-range wireless communication interface 202 may also include a Wi-Fi based chipset that allows a mobile station to serve as a Wi-Fi access point, for example, in the same manner that portable wireless devices today can be set to function as Wi-Fi access points.

Short-range wireless communication interface 202 may alternatively or additionally comprise a BLUETOOTH chipset and antennas adapted to facilitate BLUETOOTH air interface communication with other mobile stations.

Cellular communication interface 204, similarly, may comprise a cellular chipset and antennas adapted to facilitate communication with a cellular radio access network according to a protocol such as CDMA, TDMA, AMPS, or GSM, for instance. Short-range wireless communication interface 202 and cellular communication interface 204 can be integrated in whole or in part, such as in the form of an integrated chipset and/or sharing one or more antennas.

User interface 206 preferably comprises user output components such as a display screen and audio speaker, and input components such as a keypad, touch-sensitive screen, and microphone. Further, user interface 206 preferably includes circuitry for converting between analog and digital representations of voice or media, so as to facilitate communication of such media.

Processor 208 preferably comprises one or more general purpose processors and/or special purpose processors. Data storage 210 preferably includes one or more volatile and/or non-volatile storage components (e.g., magnetic, optical, or organic components) and may be integrated in whole or in part with processor 208.

As shown, data storage 210 may contain a code or codes associated with the apparatus, such as the MSP apparatus' code 122 that is associated with the MSP apparatus 118 or a patient apparatus' code that is associated with the patient apparatus 112. Further, data storage 210 may contain program instructions 212 executable by processor 208 to carry out various functions described herein, whether as patient apparatus 112 or MSP apparatus 118. For example, the program instructions 212 may be executable by the processor 208 to detect a transmission from another apparatus or a computer server and to receive and store that transmitted data in data storage 210. The program instructions 212 may be further executable to combine received data with other data stored in data storage 210 and/or to encrypt or decrypt data. Additionally, the program instructions 212 may be executable to re-transmit received data, transmit local data, or transmit combined data. For example, program instructions associated with the MSP apparatus 118 may be executable to encrypt and transmit the MSP apparatus' code 122 to the patient apparatus 112. Other program instructions associated with the patient apparatus 112 may be executable to receive the MSP apparatus' code 122, decrypt the MSP apparatus' code 122, and to form an access token 124 based on the MSP apparatus' code 122 and the patient apparatus' code. The program instructions associated with the patient apparatus 112 may then be executable to encrypt and transmit the access token 124.

The program instructions 212 may also be executable by the processor to function as a Wi-Fi access point, by broadcasting an SSID via Wi-Fi interface 202, receiving/detecting an association request from a Wi-Fi station, authenticating and otherwise establishing a Wi-Fi association with the Wi-Fi station, and acting as a DHCP server to assign local IP addresses to Wi-Fi stations that associate with it. Further, as another example, the program instructions 212 may be executable by the processor to function as a Wi-Fi client station, by detecting an SSID broadcast from an access point, sending an association request to the access point and establishing Wi-Fi association with the access point, and sending a DHCP request to receive an IP address assignment from the access point.

The program instructions 212 may also be executable by the processor to function as a BLUETOOTH master or slave device by broadcasting a device name and device class and/or allowing inquiry into the list of services provided by device 200 or by allowing BLUETOOTH pairing.

As yet another example, the program instructions may define SIP client logic for engaging in IP-based call setup signaling, such as SIP signaling, and the program instructions may define RTP client logic for facilitating RTP communication in a manner well known in the art.

3. System Operation

Referring again to FIG. 1, when patient apparatus 112 powers on or otherwise enters the coverage area of the RAN 102, the patient apparatus 112 may first register with the RAN 102. To do so, the mobile apparatus 112 may send a registration message over an air interface access channel to the RAN 102, providing the RAN 102 with an identification of the patient apparatus 112, such as a mobile identification number (MIN), a network access identifier (NAI), and/or electronic serial number (ESN) and other information. The RAN 102 may then authenticate and authorize the patient apparatus 112. Further, the RAN 102 may obtain a copy of the patient apparatus's service profile from a home location register (not shown) and store the profile in a visitor location register (VLR) (not shown) for later reference.

Once the patient apparatus 112 is registered, the patient apparatus 112 may then originate outgoing communications via the RAN 102 and receive incoming communications via the RAN 102. For instance, the patient apparatus 112 may acquire an IP address for communication on packet-switched network 110 and use that IP address to exchange packet-data with the PMI provider 103.

To engage in packet-data communication, the patient apparatus 112 would first acquire both a radio link (i.e., a traffic channel) and a data link. To do this, the patient apparatus 112 may send an origination message to the RAN 102, including in the origination message a packet-data service option code. Upon receipt of the origination message bearing that service option code, the BSC 106 may process the origination, and the BSC 106 may responsively assign a traffic channel for use by the patient apparatus 112 and may signal to the PDSN 108 to facilitate setup of packet-data connectivity. The PDSN 108 and patient apparatus 112 may then negotiate to establish a data link layer connection, such as a point-to-point protocol (PPP) session for instance, and the PDSN 108 or other network entity may assign an IP address for the patient apparatus to use on packet-switched network 110. (Other mechanisms for acquiring wireless packet data connectivity are also known and can be used instead. For instance, in an evolution data only (EvDO) based RAN, a radio network controller (RNC) may operate in a manner analogous to a BSC, and different signaling may be employed.)

Once the patient apparatus 112 acquires packet-data connectivity, the mobile apparatus may then send and receive packet-data via the PDSN 108 and the packet-switched network 110 to communicate with other packet network nodes, such as the PMI provider 103.

In the exemplary embodiment, patient medical information concerning the patient 114 would be held by, or accessible by, the PMI provider 103. For example, the PMI may be retained on a network server. The PMI provider 103 may indicate, for each patient's medical information, the patient apparatus' code, which can be provisioned into the network server at the time the patient acquires the apparatus—such as during service activation.

In the event that the patient 114 required emergency medical care, a responding medical service person 116, such as an emergency medical technician or paramedic, would be able to access the patient's medical information through the medical service person's MSP apparatus 118.

Referring again to FIG. 1, upon being placed in proximity to each other, the patient apparatus 112 and the MSP apparatus 118 would preferably seek to set up an association 120. The association 120 could be through any short-range wireless connection such as Wi-Fi or BLUETOOTH and may be a direct wireless connection between the apparatuses without the use of an intermediate device such as an independent Wi-Fi access point. The association 120 can be peer-to-peer or client-server in nature (with the MSP apparatus 118 being client or server). The attempt to set up an association may occur automatically or upon a request by the medical service person 116 or the patient 114.

As an example, the patient 114 may wish to make her medical information available through a PMI provider 103. Thus, she may cause her apparatus 112 to continuously broadcast a predefined passkey/SSID over Wi-Fi, where the predefined passkey/SSID information may be provided to the patient by the PMI provider 103 or may be automatically entered into the apparatus 112 during provisioning. The predefined passkey/SSID broadcast functionality may be part of the programming instructions present in, or provisioned into, the patient apparatus 112 and may be available to the patient 114 through a simple interface, such as a yes/no menu selection.

Later, during a potential medical emergency involving the patient 114, a medical service person 116, upon arriving at the scene, could direct his apparatus 118 to search for the predefined passkey/SSID. Once the MSP apparatus 118 sees the predefined passkey/SSID, the MSP apparatus 118 may notify the medical service person 116 via the user interface 206 by means of a visual or audio cue. The medical service person 116 could then direct his MSP apparatus 118 to set up a Wi-Fi association with the patient apparatus 112 for the purpose of eventually obtaining the patient's medical information from the PMI provider 103.

Other variations are also possible. For example, the patient apparatus 112 may not automatically broadcast the passkey/SSID. Instead, the patient, after suffering a medical emergency, may manually direct the apparatus to begin broadcasting. Also, a person could set the MSP apparatus to automatically and continuously search for the predefined passkey/SSID and/or to automatically connect to a patient apparatus 112 broadcasting the passkey/SSID without intervention by the medical service person 116. In another example, a person could set the patient apparatus 112 to manually or automatically and continuously search for a predefined passkey/SSID broadcast by the MSP apparatus 118 and to then connect to the apparatus broadcasting the passkey/SSID with or without intervention by the patient 114.

In another variant, the patient apparatus 112 could broadcast a BLUETOOTH visibility indication or pairing request to which the MSP apparatus 118 responds and connects via BLUETOOTH, or vice versa. The response and connection could be automatic or at the direction of the medical service person 116. Wi-Fi or BLUETOOTH are examples of acceptable short-range wireless communication protocols, but other protocols now known or later developed are also acceptable.

Once the association 120 is made, the MSP apparatus 118 may transmit its MSP apparatus' code 122 to the patient apparatus 112 via the direct wireless connection. Prior to any transmission, the MSP apparatus may programmatically encrypt the MSP apparatus' code 122 to prevent plain-text viewing.

Preferably, the MSP apparatus 118 may automatically transmit the MSP apparatus' code 122 following a successful association with a patient apparatus 112 using the Wi-Fi or BLUETOOTH direct wireless connection. Further, the patient apparatus 112 may be programmed to receive the MSP apparatus' code 122 following a successful association with an MSP apparatus 118. Other variations are also possible. The medical service person 116 may manually direct his MSP apparatus 118 to send the MSP apparatus' code once the association 120 is made. Alternatively, the patient apparatus 112 may automatically, or at the direction of the patient 114, transmit a request for the MSP apparatus' code 122 following a successful association 120 and the MSP apparatus 118 may then responsively transmit the MSP apparatus' code 122 automatically or upon direction by the medical service person 116.

Following receipt of the MSP apparatus' code 122, the patient apparatus 112 may then create an access token 124. As an example, program instructions 212 present on the patient apparatus may first cause the received MSP apparatus' code 122 to automatically be stored in data storage 210. Further, patient apparatus 112 may also automatically decrypt the MSP apparatus' code 122 if it was received encrypted. Next, either automatically or upon direction by a user of the patient apparatus 112, the program instructions 212 may combine the MSP apparatus' code 122 with the patient apparatus' code stored on the patient apparatus 112 so as to form the access token 124. Preferably, the program instructions 212 may create the access token 124 by appending the patient apparatus' code to the MSP apparatus' code 122, or vice-versa, in the form of a data string. Alternatively, the programming instructions 212 may cause the patient apparatus' code and the MSP apparatus' code 122 to be separately embedded in a larger data string that contains additional information. The additional information could, for example, consist of patient and/or medical service person identifiers such as names, location information such as geographic coordinates, and/or identifiers relating to the type and/or scope of patient medical information being requested such as blood type, known allergies, or general trauma information. Further, the programming instructions 212 may encrypt the access token 124 to prevent plain-text viewing. Alternatively, the programming instructions 212 may encrypt the patient apparatus' code and append or add it into a data string containing at least the already encrypted MSP apparatus' code 122, or vice-versa.

The patient apparatus 112 may then transmit the access token 124 to the PMI provider 103 via the RAN 102 WWAN connection and the packet-switched network 110. Preferably, the patient apparatus will transmit the access token 124 immediately upon successful creation of the access token. However, the program instructions may alternatively cause the patient apparatus to request approval from the user before transmitting the access token 124.

Upon receipt of the access token 124, the PMI provider 103 may preferably validate the access token 124. The PMI provider may validate the access token 124 to ensure (i) that the MSP apparatus 118 is authorized to receive the PMI data 126 and (ii) that the patient apparatus 112 is associated with the PMI data 126 requested. To validate the access token 124, software associated with the PMI provider 103 will preferably decrypt the access token 124 and parse out the patient apparatus' code and the MSP apparatus' code 122. The PMI provider 103 may then compare the patient apparatus' code against a list of valid patient apparatus' codes. The PMI provider 103 may also compare the MSP apparatus' code 122 against a list of valid MSP apparatus' codes. If both codes are present on the corresponding list, the access token may be considered validated and the PMI provider 103 may authorize transmission of patient medical information. This validation method is just an example and other validation methods are possible.

Alternatively or additionally, the PMI provider 103 may consider additional information present within the access token during the validation process. For example, certain codes may only be associated with certain types of releasable patient medical information. Therefore, the PMI provider 103 may compare the MSP apparatus' code 122 and/or the patient apparatus' code against one or more lists or databases in order to determine what patient medical information may be transmitted from the PMI provider 103.

Upon successful validation of the access token 124, the PMI provider 103 may preferably transmit PMI 126 to the patient apparatus 112 via the packet-switched network 110 and the RAN 102. The PMI provider 103 may either transmit the PMI 126 automatically upon retrieving and assembling the PMI data 126 or transmit an acknowledgement to the patient apparatus that it has validated the access token and that it will transmit the PMI 126 upon request. Prior to any transmission, software associated with the PMI provider 103 may encrypt the PMI 126 so as to prevent plain-text viewing.

Upon receipt of an automatic transmission of PMI 126 or upon requesting and receiving PMI 126, the patient apparatus 112 may transmit the received PMI to the MSP apparatus 118 via the short-range direct wireless connection. If the PMI 126 is encrypted, the MSP apparatus 118 may then apply a decryption key to decrypt the received medical information. Preferably, the MSP apparatus 118 will then present the medical information to the medical service person 116 for use in serving the patient 114.

Figure 3:
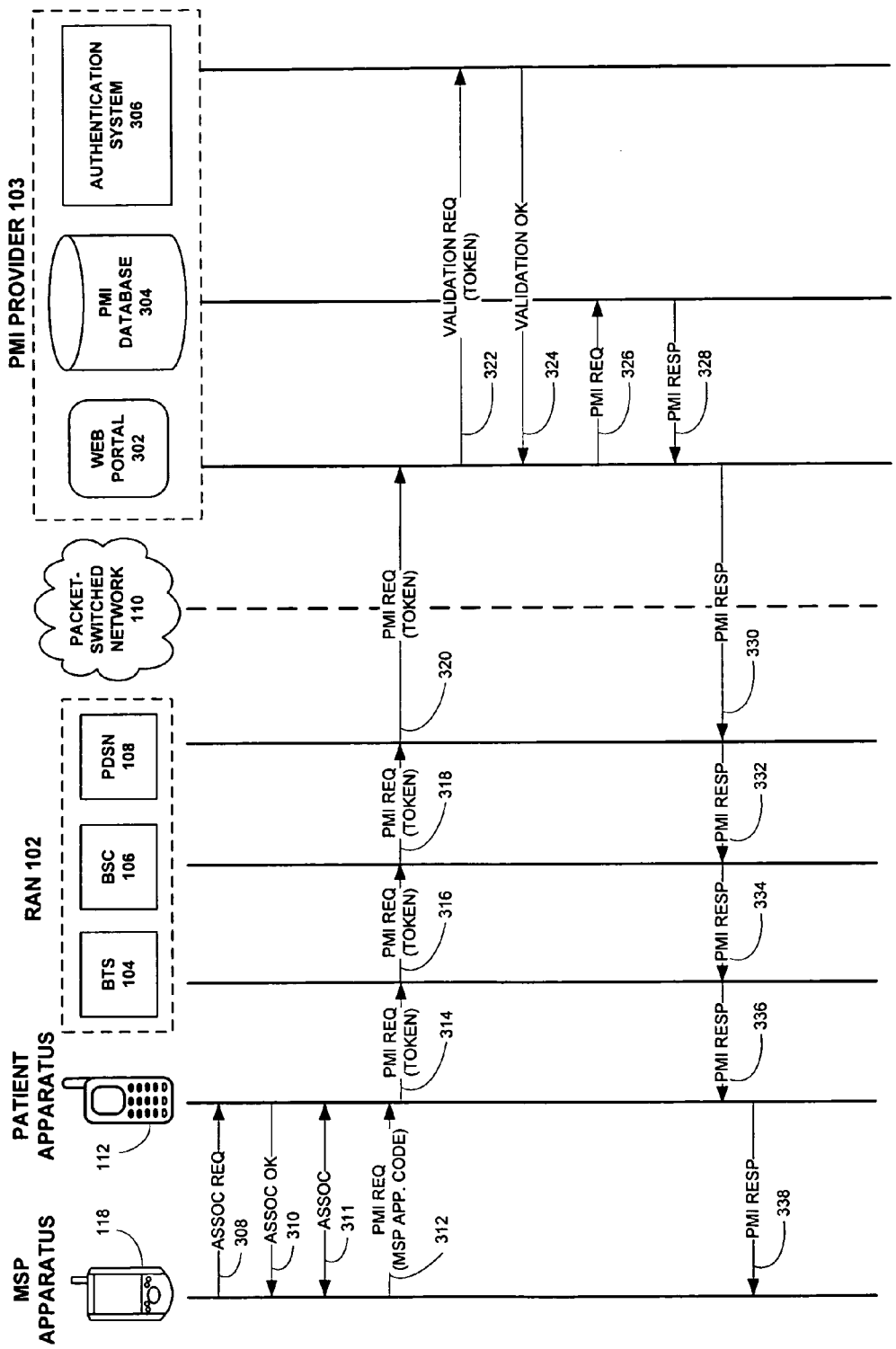
FIG. 3 is a simplified message flow diagram depicting communications regarding medical information.

FIG. 3 is a message flow diagram depicting communications regarding medical information, in accordance with an exemplary embodiment of the invention. As shown in FIG. 3, at step 308, the MSP apparatus 118 requests association with the patient apparatus 112. This may be in response to an SSID/passkey broadcast or a BLUETOOTH pairing and/or availability broadcast by the patient apparatus 112. At step 310, in response to the association request at step 308, the patient apparatus 112 authorizes an association between the patient apparatus 112 and the MSP apparatus 118. At step 311, the devices thus form an association through a short range direct wireless connection such as Wi-Fi or BLUETOOTH.

In an alternative association setup not shown, the patient apparatus 112 may request association with the MSP apparatus 118, and the MSP apparatus 118 may authorize the association. Further, the association request from the patient apparatus 112 may be in response to an SSID/passkey broadcast or a BLUETOOTH pairing and/or availability broadcast by the MSP apparatus 118.

At step 312, the MSP apparatus 118 sends a request for PMI. Preferably, the MSP apparatus 118 may send the request for PMI automatically upon accomplishment of the association 120. Alternatively, the MSP apparatus may wait for user direction to transmit the request for PMI. Included in the PMI request, the MSP apparatus 118 incorporates the MSP apparatus' code 122 for purposes of eventual inclusion in the access token 124. Alternatively, the MSP apparatus 118 may send the MSP apparatus' code 122 to the patient apparatus 112 in a communication separate from the request for PMI. In another alternative, the MSP apparatus 118 may send no explicit request for PMI and may send only the MSP apparatus' code 122, which the patient apparatus 112 may be programmed to interpret as a de facto request for PMI.

Upon receiving the MSP apparatus' code 122, the patient apparatus 112 combines the MSP apparatus' code with a patient apparatus' code to form an access token. As previously stated, the program instructions 212 within the patient apparatus 112 may create the access token 124 by appending the patient apparatus' code to the MSP apparatus' code 122, or vice-versa, in the form of a data string. Alternatively, the program instructions 212 may cause the patient apparatus' code and the MSP apparatus' code 122 to be separately embedded in a larger data string that contains additional information.

At step 314, the patient apparatus 112 transmits the PMI request to the BTS 104 via a WWAN link. The PMI request may consist of only the access token 124, where the PMI provider 103 is programmatically adapted to consider the receipt of the bare access token 124 as a request for PMI. Alternatively, the PMI request may consist of additional information, such as requests for specific patient medical information, in which case, the patient apparatus may embed the access token 124 within the larger message containing the PMI request. As another alternative, the access token 124 may be broadcast separate from a PMI request, where the PMI provider 103 is programmatically adapted to await a PMI request upon the receipt of a bare access token 124, or vice-versa. For purposes of explanation only, and not as a limitation, any subsequent reference to a PMI request traceable to a PMI request originally sent from the patient apparatus 112 should be read as if the referenced PMI request includes the access token 124.

At steps 316 and 318, the PMI request is passed from the BTS to the BSC and from the BSC to the PDSN, respectively. At the PDSN, the PDSN may convert the PMI request data into a format suitable for transport over the packet-switched network 110, such as a packet-data format. The PDSN then transmits the PMI request via the packet-switched network 110 to the web portal 302 of the PMI provider 103 at step 320. This transmission may be in the form of an HTTP GET or HTTP POST request message which includes the access token 124. Upon receipt of the PMI request, the web portal 302 then transmits the access token 124 to the authentication system 306 at step 322 and requests validation of the access token in order to provide PMI in response to the PMI request. Prior to transmission, the web portal 302 may parse out the access token 124 if it is part of a larger PMI request message.

If the authentication system 306 validates the access token, then the authentication system 306 may transmit the validation response to the web portal 302 at step 324. As previously described, the authentication system 306 may, for example, validate the access token by parsing out the MSP apparatus' code 122 and the patient apparatus' code and comparing those codes to a list of known valid codes.

At step 326, the web portal 302 may request PMI from the PMI database 304. The PMI database 304 contains medical information associated with the patient and/or the patient's apparatus and intended for delivery to medical service personnel. The web portal's request for PMI at step 326 may occur after, before, or simultaneous to the validation request at step 322. Once validation has been provided at step 324, the PMI database 304 may, at step 328, provide patient medical information to the web portal 302 responsive to the request for PMI. The web portal may include program logic to encrypt the PMI information in anticipation of transmitting the PMI outside of the PMI provider 103.

At step 330, the PMI response is delivered via the packet-switched network 110 to the PDSN 108. At steps 332 and 334, the PMI response is passed from the PDSN 108 to the BSC 106 and to the BTS 104, respectively. Following receipt at the BTS, 104 the PMI response is delivered from the BTS 104 to the patient apparatus 112 via a WWAN link at step 326.

Upon receipt of the PMI response, the patient apparatus 112 may transmit the PMI to the MSP apparatus 118 over the short-range direct wireless connection and via the existing association 120. The patient apparatus 112 may transmit the PMI automatically upon receipt of the PMI or, alternatively, the patient apparatus 112 may notify the patient apparatus that it has PMI and then transmit the PMI only in response to a send request by the MSP apparatus 118. The MSP apparatus 118 may then programmatically apply a decryption key and decrypt and display the PMI.

4. Conclusion

An exemplary embodiment of the present invention has been described above. Those skilled in the art will understand, however, that changes and modifications may be made to this embodiment without departing from the true scope and spirit of the present invention, which is defined by the claims.

To illustrate, although the foregoing description focuses on conveying patient medical information solely from a remote PMI provider, the invention can be extended to include transmitting, directly from the patient apparatus, medical information that is stored locally on the patient apparatus. For example, while the patient apparatus 112 is sending the access token 124 in order to request PMI from the PMI provider 103, the patient apparatus could also be retrieving medical information stored in its own data storage and immediately transmitting that medical information to the MSP apparatus 118 as a form of supplementary PMI.

Other examples are possible as well.

We claim:

1. A method of conveying medical information regarding a patient from a network server, via a first apparatus possessed by the patient to a second apparatus possessed by a medical service person, the method comprising:
    receiving at the network server, via a cellular wireless connection from the first apparatus, a combination of (i) a first code that is associated with the first apparatus and that is stored on the first apparatus and (ii) a second code that is associated with the second apparatus and that the first apparatus received via a direct wireless connection from the second apparatus;
    at the network server, using the combination as a basis to authorize transmission of the medical information to the first apparatus; and
    at the network server, upon successful authorization of transmission of the medical information to the first apparatus, transmitting the medical information in an encrypted form to the first apparatus via the cellular wireless connection, for transmission of the medical information in turn from the first apparatus to the second apparatus via the direct wireless connection, for decryption and presentation to the medical service person of the medical information in turn by the second apparatus,
    wherein the second apparatus has a decryption key that enables decryption and presentation of the medical information, and
    wherein the first apparatus does not have a decryption key that enables decryption and presentation of the medical information.

2. The method of claim 1, wherein the first apparatus is a cell phone.

3. The method of claim 2, wherein the direct wireless connection comprises a connection selected from the group consisting of a BLUETOOTH connection and a Wi-Fi connection.

4. The method of claim 1, wherein the direct wireless connection is established when the second apparatus is in proximity to the first apparatus, and wherein the second code is conveyed from the second apparatus to the first apparatus after establishment of the direct wireless connection.

5. The method of claim 4, wherein the second apparatus seeks to establish the direct wireless connection with the first apparatus in response to a request from the medical service person.

6. The method of claim 1, wherein the combination is established by the first apparatus by a process comprising combining and encrypting the first code and the second code.

7. The method of claim 1, wherein using the combination as a basis to authorize transmission of the medical information to the first apparatus comprises:
    obtaining the first code from the combination, and validating the first code;
    obtaining the second code from the combination, and validating the second code; and
    authorizing the transmission in response to successful validation of the first code and successful validation of the second code.

8. The method of claim 1, wherein the decryption key that the second apparatus has is a master decryption key usable by the second apparatus to decrypt medical information regarding various patients.

9. A portable communication device possessed by a patient and usable for conveying medical information regarding the patient from a network server to an apparatus possessed by a medical service person, the portable communication device comprising:
    a first wireless communication interface operable to engage in direct wireless communication;
    a second wireless communication interface operable to engage in cellular wireless communication;
    a processor;
    data storage;
    device data stored in the data storage and associated with the portable communication device; and
    program logic stored in the data storage and executable by the processor (a) to receive apparatus data via the first wireless communication interface from the apparatus, the apparatus data being associated with the apparatus, (b) to send a combination of the device data and the apparatus data via the second wireless communication interface to the network server, (c) to then receive the medical information in an encrypted form via the second wireless communication interface from the network server, the network server having first used the combination to authorize transmission of the medical information to the portable communication device, and (d) to send the received medical information via the first wireless communication interface to the apparatus for decryption and presentation of the medical information in turn by the apparatus to the medical service person,
    wherein the apparatus has a decryption key that enables decryption and presentation of the medical information, and
    wherein the portable communication device does not have a decryption key that enables decryption and presentation of the medical information.

10. The portable communication device of claim 9, wherein the portable communication device is a cell phone.

11. The portable communication device of claim 9, wherein the direct wireless communication comprises a type of communication selected from the group consisting of BLUETOOTH communication and Wi-Fi communication.

12. The portable communication device of claim 9, wherein the program logic is executable to request the apparatus data from the apparatus after a direct wireless association is established between the portable communication device and the apparatus, and wherein the program logic is executable to receive the apparatus data in response to the request.

13. The portable communication device of claim 9, wherein the program logic is further executable to establish the combination by a process comprising combining and encrypting the apparatus data and the device data.

14. A method of conveying medical information regarding a patient, via a first apparatus possessed by the patient to a second apparatus possessed by a medical service person, wherein the first apparatus stores a first code associated with the first apparatus and the second apparatus stores a second code associated with the second apparatus, the method comprising:
    establishing a direct wireless connection between the first apparatus and the second apparatus;
    conveying the second code from the second apparatus to the first apparatus, via the direct wireless connection;
    conveying a combination of the second code and first code from the first apparatus to a network server, via a cellular wireless connection;
    at the network server, using the combination as a basis to authorize transmission of the medical information, and, upon successful authorization, transmitting the medical information in an encrypted form to the first apparatus via the cellular wireless connection; and
    upon receipt by the first apparatus of the medical information transmitted from the network server, conveying the medical information from the first apparatus to the second apparatus via the direct wireless connection, for decryption and presentation of the medical information in turn by the second apparatus to the medical service person,
    wherein the second apparatus has a decryption key that enables decryption and presentation of the medical information, and
    wherein the first apparatus does not have a decryption key that enables decryption and presentation of the medical information.

15. The method of claim 14, wherein the first apparatus is a cell phone.

16. The method of claim 14, wherein using the combination as a basis to authorize transmission of the medical information comprises:
    obtaining the first code from the combination, and validating the first code;
    obtaining the second code from the combination, and validating the second code; and
    successfully authorizing the transmission in response to successful validation of the first code and successful validation of the second code.

17. The method of claim 14, further comprising conveying from the first apparatus to the second apparatus additional medical information regarding the patient, wherein the additional medical information is stored on the first apparatus and is not received by the first apparatus from the network server.

* * * * *